United States Patent
Lin et al.

(10) Patent No.: US 8,873,034 B2
(45) Date of Patent: Oct. 28, 2014

(54) FIBER-TYPE IMAGE CAPTURING METHOD AND APPARATUS THEREOF

(71) Applicants: China Medical University, Taichung (TW); Industrial Technology Research Institute, Hsinchu County (TW)

(72) Inventors: Shinn-Zong Lin, Taichung (TW); Horng-Jyh Harn, New Taipei (TW); Rung-Ywan Tsai, Taoyuan County (TW); Yuan-Chin Lee, Hsinchu (TW)

(73) Assignees: China Medical University, Taichung (TW); Industrial Technology Research Institute, Hsinchu County (TW)

( * ) Notice: Subject to any disclaimer, the term of this patent is extended or adjusted under 35 U.S.C. 154(b) by 0 days.

(21) Appl. No.: 13/846,821

(22) Filed: Mar. 18, 2013

(65) Prior Publication Data

US 2014/0168654 A1  Jun. 19, 2014

(30) Foreign Application Priority Data

Dec. 19, 2012  (TW) .............................. 101148364 A (51) Int. Cl.
*G01N 21/47*  (2006.01)

(52) U.S. Cl.
CPC .................................. *G01N 21/474* (2013.01)
USPC ......................................... 356/246; 356/446

(58) Field of Classification Search
CPC .................................................... G01N 21/47
USPC .................... 356/246, 39–41, 35.5, 479, 446; 600/478; 385/33, 11, 31, 100, 109
See application file for complete search history.

(56) References Cited

U.S. PATENT DOCUMENTS

| | | | | |
|---|---|---|---|---|
| 6,501,551 B1 * | 12/2002 | Tearney et al. | ............... | 356/477 |
| 6,687,010 B1 * | 2/2004 | Horii et al. | ..................... | 356/479 |
| 7,538,859 B2 * | 5/2009 | Tearney et al. | .............. | 356/35.5 |
| 7,706,646 B2 * | 4/2010 | Wang et al. | ...................... | 385/33 |
| 2010/0198081 A1 * | 8/2010 | Hanlin et al. | ................. | 600/478 |
| 2013/0338510 A1 * | 12/2013 | Tearney et al. | ............... | 600/478 |

OTHER PUBLICATIONS

In vivo endoscopic optical coherence tomography by use of a rotational microelectromechanical system probe.
In vivo three-dimensional spectral domain endoscopic optical coherence tomography using a microelectromechanical system mirror.
Optical coherence tomography in the diagnosis and treatment of neurological disorders.
Paired-angle-rotation scanning optical coherence tomography forward-imaging probe.
Power-efficient nonreciprocal interferometer and linear-scanning fiber-optic catheter for optical coherence tomography.

* cited by examiner

*Primary Examiner* — Sang Nguyen
(74) *Attorney, Agent, or Firm* — CKC Partners Co., Ltd.

(57) ABSTRACT

A fiber-type image capturing apparatus includes a fiber optic, an optical rotating module, an outer tube, an air inlet hole, and an air outlet hole. The optical rotating module is connected to one end of the fiber optic and has a light forward exit and a light lateral exit. The optical rotating module further includes a stator, a rotor, and a light path selector. The stator is fixed correspondingly to the fiber optic. The rotor has a fan blade which is pivotally connected to the stator. The light path selector is installed at the rotor and has a forward scanning path and a lateral scanning path. The outer tube fixes the fiber optic and the optical rotating module. The air inlet hole is disposed at the outer tube and feeds the fan blade with air. The air outlet hole is disposed at the outer tube and vents the air.

16 Claims, 6 Drawing Sheets

FIBER-TYPE IMAGE CAPTURING METHOD AND APPARATUS THEREOF

RELATED APPLICATIONS

This application claims priority to Taiwan Application Serial Number 101148364, filed Dec. 19, 2012, which is herein incorporated by reference.

BACKGROUND

1. Field of Disclosure

The present disclosure relates to an image capturing method. More particularly, the present disclosure relates to a fiber-type image capturing method and an apparatus of the fiber-type image capturing.

2. Description of Related Art

A probe for endoscopes, optical coherence tomography (OCT), or microscopes, needs to be small in size and preferably to be capable of remotely inspecting. Fiber optic probe is the probe with above merits.

However, almost all the conventional fiber optic probes can only conduct lateral scanning. Most fiber optic probes which are capable of forward scanning can do forward scanning only, instead of both forward and lateral scanning. However, either of these scanning approaches, forward scanning or lateral scanning, have some shortcomings. Taking the fiber optic probe of the OCT as an example, an explanation is provided below.

For a lateral-scanning fiber optic probe of the OCT system, since the user can only obtain the lateral image information rather than the forward image information, to obtain the forward image information, the user needs to further stretch the probe in enough depth and then pull it back in a spiral manner. So the user can scan the tissue spirally along with the lateral-scanning approach, to obtain some forward scanning information. But there are risks using this approach for lack of sufficient information in front of the probe during medical examination. Further, because the tip of the probe is usually still several millimeters away from the center of the reflecting surface of the OCT system, the tip of the probe requires several millimeters in advance of the scanning spot of interest, which is not always feasible in implementation.

As to the traditional forward scanning probe, it on the other hand cannot obtain the lateral image information. In need of the lateral image information, the forward scanning probe has to be pulled back and switched to the lateral scanning probe so as to go on the lateral scanning. This approach is time and money inefficient, which increase the operating cost.

SUMMARY

Given the above, a fiber-type image capturing method is provided which includes the following steps. A light beam with a predetermined wavelength is selected. The light beam passes through a forward scanning path, a lateral scanning path, or both the forward scanning path and the lateral scanning path simultaneously, based on the predetermined wavelength of the light beam. The forward scanning path, the lateral scanning path, or both the forward scanning path and the lateral scanning path simultaneously is/are rotated. The light beam illuminates a sample to be scanned. The scattered light from the scanned sample is collected.

According to one embodiment of the present disclosure, the forward scanning path is through optical refraction. The lateral scanning path is through optical reflection. The light beam passing through both the forward scanning path and the lateral scanning path simultaneously resulted from the light beam passing through optical refraction and optical reflection simultaneously.

A fiber-type image capturing apparatus, applied to the foregoing fiber-type image capture method, is also provided. The fiber type image capturing apparatus comprises a fiber optic, an optical rotating module, an outer tube, an air inlet hole, and an air outlet hole. The optical rotating module is connected to one end of the fiber optic. The optical rotating module has a light forward exit and a light lateral exit. The optical rotating module comprises a stator, a rotor, and a light path selector. The stator is fixed correspondingly to the fiber optic. The rotor has a fan blade, and the fan blade is pivotally connected to the stator. The light path selector is installed at the rotor. The light path selector has a forward scanning path and a lateral scanning path. The outer tube wraps or fixes the fiber optic and the optical rotating module. The air inlet hole is disposed at the outer tube and feeds the fan blade with air. The air outlet hole is disposed at the outer tube and vents the air fed by the air inlet hole.

According to one embodiment of the present disclosure, the fiber optic is single mode fiber optic. And the fiber optic can be a fiber optic bundle or one single fiber. The light path selector is a plate having two opposite surfaces, and an included angle between the two surfaces is less than or equal to 10 degrees. The light path selector has a film coating and can transmit light. The light path selector guides the inputted light beam within the predetermined wavelength band to the light forward exit by refraction. And the light path selector guides the inputted light beam within another predetermined wavelength band to the light lateral exit by reflection. The fiber-type image capturing apparatus can further comprise a focusing module. The focusing module is located between the fiber optic and the optical rotating module, for eliminating the aberration. The focusing module may be spherical lens, aspheric lens, gradient-index lens, or micro-lens. And the focusing module can be integrated with the fiber optic.

According to another embodiment of the present disclosure, the fiber-type image capturing apparatus can further comprise a coil group and at least one magnet. The coil group is located around the light path selector. For example, the coil group can be located between the optical rotating module and the outer tube, or the coil group can be located between the light path selector and the rotor. The magnet is located at an end surface of the light path selector. When the coil group is supplied with current, the magnetic field thus created can exert force to the magnet to rotate the light path selector to be tilt to a desired angle. By controlling the current, the tilt angle of the light path selector can be controlled, hence a refraction angle of the light path selector can be controlled.

The foregoing fiber-type image capturing apparatus can further include a stationary shaft, a fiber optic housing, or a fixing structure. The stationary shaft can be fixed to the rotor, and the light path selector can be pivotally connected to the stationary shaft to be installed at the rotor. The fiber optic can be disposed in the fiber optic housing. And the fixing structure can fix the fiber optic and the fiber optic housing to the outer tube.

When performing forward scanning, a user can input the light beam with a predetermined wavelength band so that the light beam can pass the light path selector through refraction. Because the light path selector is a plate and because of Snell's law, when the light beam passing through the path selector, the optical axis of the refracted light beam will be parallel with that of the original inputted light beam, with an offset. So when the air inlet hole feeds the fan blade with air to rotate the rotor and the light path selector, the user can perform forward circular scanning path and obtain the forward scanning information. Then the user can apply electric current to the coil group to control the tilt angle of the light path selector while the rotor is rotating. Because of Snell's law, when the angle between the light path selector and the inputted light beam is changed, the offset distance between the refracted light beam and the inputted light beam is changed accordingly. So the radius of the forward circular scanning path is changed subsequently. Using the fiber-type image capturing apparatus according to the embodiment of the present disclosure as the probe of optical coherence tomography, since optical coherence tomography is able to provide depth resolution, a cylinder scanning with depth information of forward scanning can be obtained as a result.

When performing lateral scanning, a user can input the light beam with another predetermined wavelength band so that the light beam can be transmitted by the light path selector through reflection. The angle between the light path selector and the rotor can be fixed, and the air inlet hole feeds the fan blade with air, so circular scanning information of lateral scanning can be obtained. Then, the user can move the fiber-type image capturing apparatus forward or backward, so that cylinder scanning information of lateral scanning can be obtained. Since optical coherence tomography is able to provide depth resolution, a hollowly cylinder scanning with depth information of lateral scanning can be obtained as a result.

When performing forward and lateral scanning simultaneously, a user can input the light beam with predetermined wavelengths bands, so that the light beam can be transmitted by the light path selector partially through refraction and partially through reflection. According to the embodiment of the present disclosure, the fiber-type image capturing apparatus has a light forward exit and a light lateral exit. Therefore, applying the same forward scanning process and the lateral scanning process simultaneously as foregoing, a user can perform the forward scanning and the lateral scanning simultaneously.

To sum up, a probe applied the fiber-type image capturing apparatus according to embodiments of the present disclosure can obtain both forward and lateral scanning information using only one probe. The back-end image process can therefore produce scanning image with depth information. And the end of the probe doesn't need to be any farther in front of the scanning spot to obtain the forward scanning information. The probe needs not to be changed to another probe to obtain the later scanning information either. Using only one probe can perform both forward scanning and lateral scanning. Applying present disclosure can save operating time, and moreover, simplify the system.

It is to be understood that both the foregoing general description and the following detailed description are by examples, and are intended to provide further explanation of the disclosure as claimed.

BRIEF DESCRIPTION OF THE DRAWINGS

The disclosure can be more fully understood by reading the following detailed description of the embodiment, with reference made to the accompanying drawings as follows.

DETAILED DESCRIPTION

Reference will now be made in detail to the present embodiments of the disclosure, examples of which are illustrated in the accompanying drawings. Wherever possible, the same reference numbers are used in the drawings and the description to refer to the same or like parts.

Figure 1:
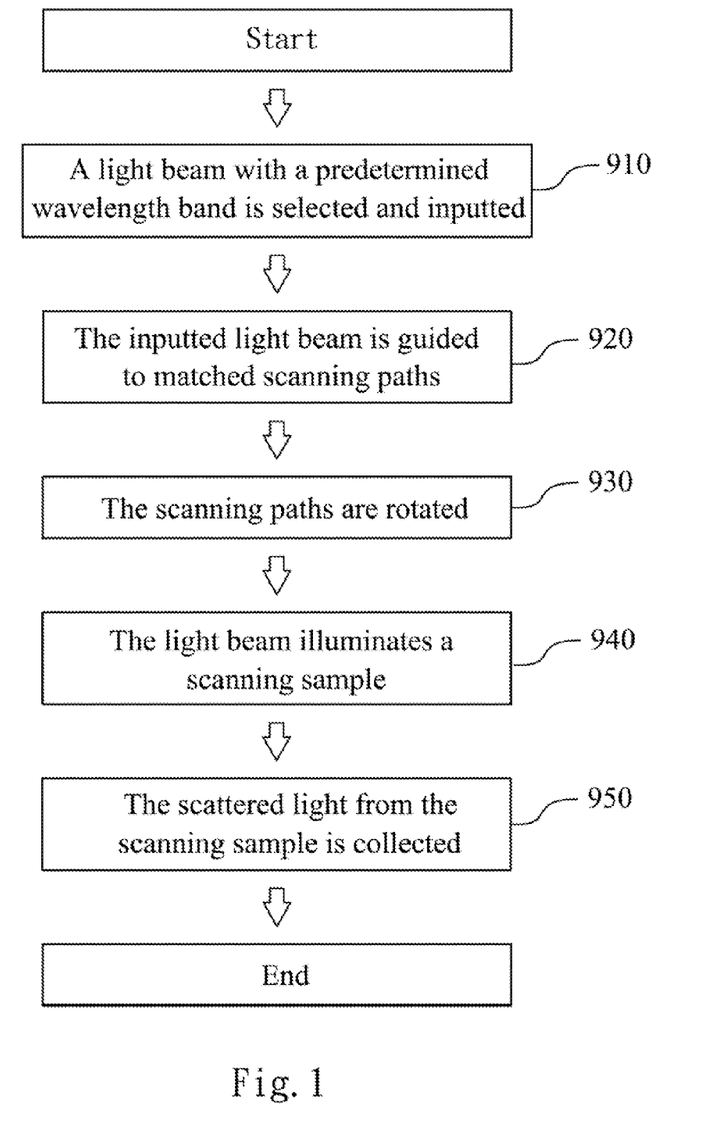
FIG. 1 is a flowchart showing a fiber-type image capturing method according to one embodiment of the present disclosure.

FIG. 1 is a flowchart showing a fiber-type image capturing method according to one embodiment of the present disclosure. In FIG. 1, the fiber-type image capturing method includes the following steps. In step 910, a light beam with a predetermined wavelength band is selected and inputted. In step 920, the inputted light beam is guided to matched paths. More specifically, the light beam with wavelength band predetermined to perform forward scanning is guided to a forward scanning path, and the light beam with wavelength band predetermined to perform later scanning is guided to a lateral scanning path. In step 930, the forward scanning path and the lateral scanning are rotated. In step 940, the light beam illuminates a scanning sample. In step 950, the scattered light from the scanning sample is collected. At back-end, an image process system can be connected, to produce a tissue scanning image with depth information using the collected scattered light.

Figure 2:
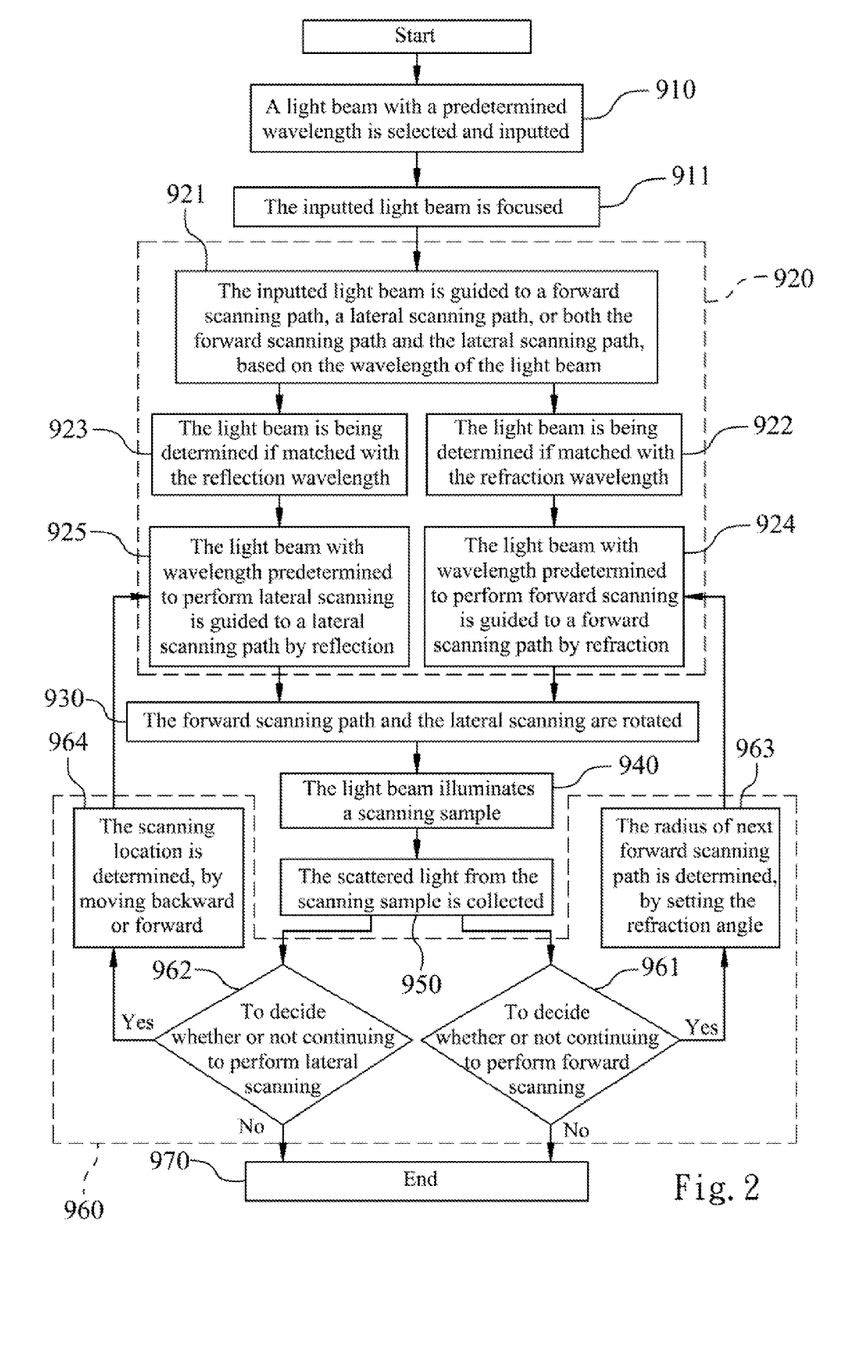
FIG. 2 is a flowchart showing a fiber-type image capturing method according to another embodiment of the present disclosure.

FIG. 2 is a flowchart showing a fiber-type image capturing method according to another embodiment of the present disclosure. Additional to the foregoing embodiment of FIG. 1, a step 911 and a step 960 are added.

In step 910, a light beam with a predetermined wavelength band is selected and inputted. In step 911, the inputted light beam is focused. Step 920 includes steps 921 to 925. In step 921, the inputted light beam is guided to a forward scanning path, a lateral scanning path, or both the forward scanning path and the lateral scanning path, based on the wavelength of the light beam. In step 922, the light beam is being determined if matched with the refraction wavelength band. If the result of step 922 is positive, then proceed with step 924. In step 924, the light beam with wavelength band predetermined to perform forward scanning is guided to a forward scanning path by refraction. In step 923, the light beam is being determined if matched with the reflection wavelength band. If the result of step 923 is positive, then proceed with step 925. In step 925, the light beam with wavelength predetermined to perform lateral scanning is guided to a lateral scanning path by reflection. In step 930, the forward scanning path and the lateral scanning are rotated. In step 940, the light beam illuminates a sample. In step 950 the scattered light from the sample is collected.

In step 960, the forward scanning or the lateral scanning can be performed iteratively, so a more detailed scanning image can be produced after scanning. Step 960 can be performed by system automatically or can be performed by the user manually. Step 960 further includes steps 961 to 964. In step 961 decides whether or not continuing to perform forward scanning. If the result of step 961 is positive, then proceeds step 963. In step 963, the radius of next forward scanning path is determined, by setting the refraction angle. After step 963, back to step 924 to perform next forward scanning. In step 962, decides whether or not continuing to perform lateral scanning. If the result of step 962 is positive, then proceeds step 964. In step 964, the scanning location is determined, by moving backward or forward. After step 964, back to step 925 to perform next lateral scanning. In step 970, the fiber-type image capturing is completed. The scattered light can then be transmitted back to back-end to produce a tissue scanning image with depth information.

Figure 3:
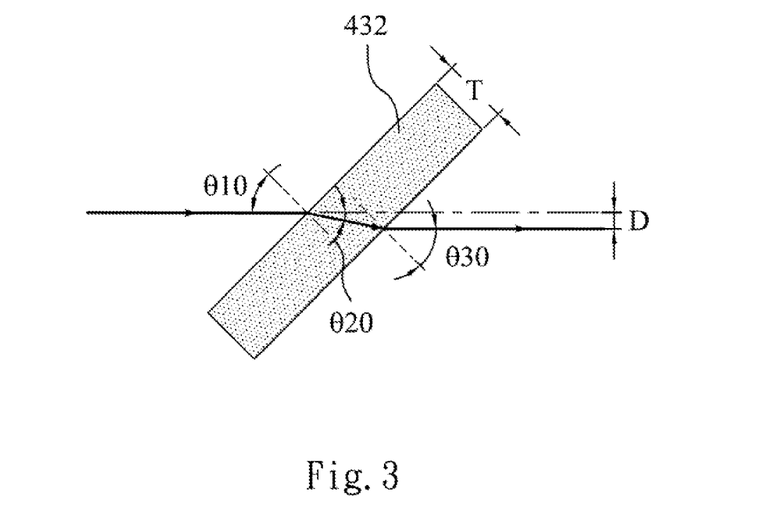
FIG. 3 is a schematic diagram of a light beam passing through a parallel plate with refraction with an offset distance D.

FIG. 3 is a schematic diagram of a light beam passing through a parallel plate 432 with refraction with an offset distance D. The parallel plate 432 is a plate with its two opposite surfaces parallel. The thickness of parallel plate 432 is T, and the refraction index of parallel plate 432 is N. When the light beam enters one surface of the parallel plate 432 with a incidence angle θ10, because of Snell's law, a refraction angle θ20 would be: θ20=(sin(θ10)/N).

And since the refraction index N is normally greater than 1, the refraction angle θ20 would be smaller than incidence angle θ10. When the light beam exits the other surface of the parallel plate 432, the light beam is refracted, again. Again, because of Snell's law, an exit angle θ30 would be the same as the incidence angle θ10. In other words, a refracted light beam would be parallel with the original inputted light beam, with an offset distance D. The offset distance D is:

$$D=T*\sin(\theta 10)-T*(1/N)*(\tan(\theta 10)-1/(1-\sin 2(\theta 10)/N2)1/2).$$

For example, when the thickness T of the parallel plate 432 is 1 mm, the refraction index N is 1.5, and the incidence angle θ10 is 45 degrees, the offset distance D would be 3.340 mm.

Figure 4:
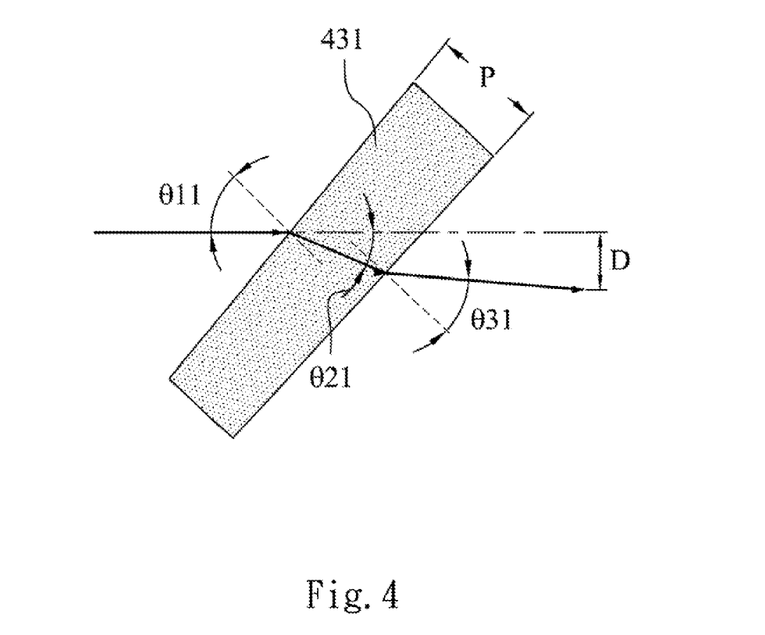
FIG. 4 is a schematic diagram of a light beam passing through a non-parallel plate with refraction with an offset distance D.

FIG. 4 is a schematic diagram of a light beam passing through a non-parallel plate 431 with refraction with an offset distance D. The Non-parallel plate 431 has an included angle P between its two opposite surfaces. Because of Snell's law, when the light beam enters the non-parallel plate 431 with an incidence angle θ11, there is a refraction angle θ21 produced, then the light beam exits the non-parallel plate 431 with an exit angle θ31. So there is an offset distance D between the refracted light beam and the original inputted light beam. And because the exit angle θ31 is not as same as the incidence angle θ11, the offset distance D is not a constant and will cause optical aberration or image distortion. However, when the included angle P is between 0 to 10 degrees, usually the optical aberration is not too serious and can be accepted.

Figure 5:
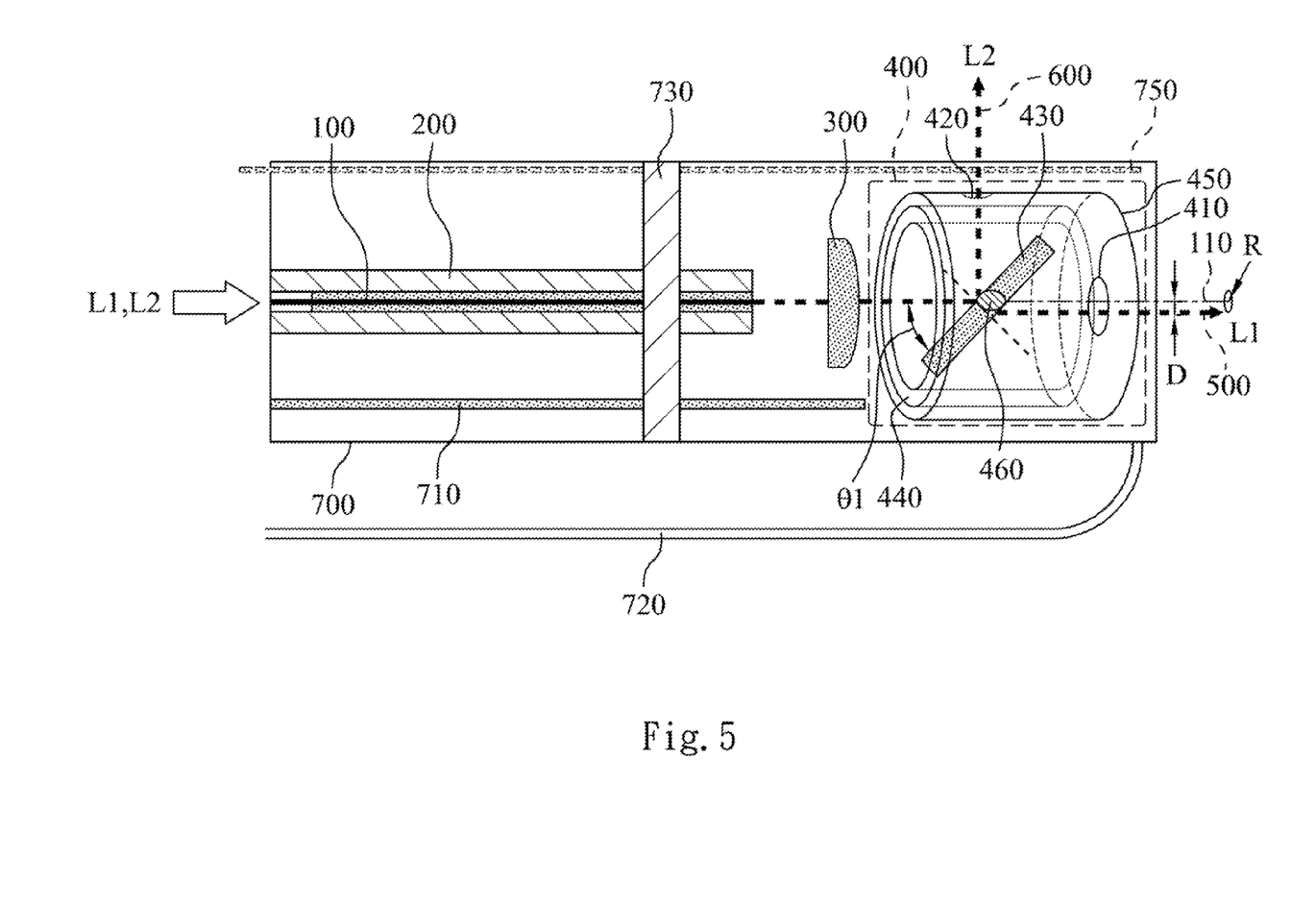
FIG. 5 is a side view of a fiber-type image capturing apparatus according to one embodiment of the present disclosure.

FIG. 5 is a side view of a fiber-type image capturer according to another embodiment of the present disclosure. The fiber-type image capturer includes a single mode fiber optic 100, a fiber optic housing 200, a focusing module 300, an optical rotating module 400, a forward scanning path 500, a lateral scanning path 600, and an outer tube 700. The single mode fiber optic 100 is for transmitting optical signal. The fiber optic housing 200 is for strengthen and fixing the single mode fiber optic 100. When a light beam coupled with a wavelength L1 and a wavelength L2 is inputted into one end of the single mode fiber optic 100, the single mode fiber optic 100 transmits the light beam. After exiting from the other end of the single mode fiber optic 100, the light beam enters the focusing module 300. The focusing module 300 can be a focusing lens group. Passing through the focusing module 300, the light beam is focused. Then the focused light beam enters the optical rotating module 400 along a base axis 110.

In detail, the optical rotating module 400 has a light forward exit 410 and a light lateral exit 420. The light forward exit 410 is located at the end of the optical rotating module 400 opposite to the other end where the light beam is inputted. The light forward exit 410 is an opening where the light beam can pass through, so that the fiber-type image capturer can proceed the forward scanning along path 500. The light lateral exit 420 is located at the side of the optical rotating module 400. The light lateral exit 420 is an opening where the light beam can pass through, so that the fiber-type image capturer can proceed the lateral scanning along path 600. The optical rotating module 400 further includes a light path selector 430, a rotor 440, and a stator 450. The light path selector 430 can be a parallel plate as the parallel plate 432 shown in FIG. 3, or be a non-parallel plate with an included angle between 0 to 10 degrees as the non-parallel plate 431 shown in FIG. 4. The light path selector 430 is installed at the rotor 440 by pivotally connected to a stationary shaft 460. The stator 450 is fixed to the outer tube 700. The outer tube 700 wraps the single mode fiber optic 100 and the optical rotating module 400.

The operation of the foregoing embodiment is described as below. The light path selector 430 is a plate with a beam-split film coated. So the light beam with wavelength L1 can pass through the light path selector 430 by refraction, and the light beam with wavelength L2 can be reflected from the light path selector 430. When entering the optical rotating module 400, the light beam first enters the light path selector 430. Because of Snell's law and the principle shown in FIG. 3 and FIG. 4, the light beam with wavelength L1 can pass through the light path selector 430 with an offset distance D. If the optical rotating module 400 rotates along the base axis 110, then the offset distance D becomes the radius of the forward scanning path 500. The focused light beam with wavelength L1 thus can perform forward scanning, by passing through the light forward exit 410, passing along the forward scanning path 500, and then focusing on a scanning sample. In a similar way, the focused light beam with wavelength L2 thus can perform lateral scanning, by passing through the light lateral exit 420, passing along the lateral scanning path 600, and then focusing on a scanning sample.

Moreover, the optical rotating module 400 is a fan structure with hollow core. The fiber-type image captures can further include an air inlet tube 710 and an air outlet tube 720. The air inlet tube 710 can feeds the fan blade of the rotor 440 with air to make the rotor 440 rotate. The rotor 440 rotates with the light path selector 430. The air outlet tube 720 is connected to an air outlet hole disposed at the outer tube opposite to the optical rotating module 400. The air outlet tube 720 is for venting the air fed by the air inlet tube 710. So the air feeding of the air inlet tube 710 and the rotation of the optical rotating module 400 can both be stable. Because the air flow fed by the air inlet tube 710 relates to the rotation speed of the rotating module 400, therefore, the angular speed of the forward scanning can be controlled through controlling the air flow fed by the air inlet tube 710.

When performing forward scanning along path 500, feeding air through the air inlet tube 710 can result in a circular forward scanning path 500 with a radius R. The radius R relates to the offset distance D, as shown in FIG. 3 and FIG. 4. The offset distance D relates to the material of the light path selector 430, and relates to a predetermined angle θ1 between the light path selector 430 and the base axis 110. Changing the predetermined angle θ1 can change the radius R of the forward scanning path 500.

When performing lateral scanning along path 600, the focused light beam with wavelength L2 will be reflected from the light path selector 430 and perform lateral scanning. If the predetermined angle θ1 is 45 degrees, then the reflected light beam with wavelength L2 will be focused perpendicularly to the base axis 110 on lateral scanning sample. At this time, when the air inlet tube 710 feeds air into the rotating module 400, the rotating module 400 rotates stably and the lateral scanning can be completed. During lateral scanning, keeping the predetermined angle θ1 of the light path selector 430 stable and accurate can avoid additional optical aberration due to asymmetry. But there is some tolerances, the tolerance within about 0 to 10 degrees can still be acceptable. The foregoing embodiment can further includes a moving mechanism (not shown) to bring the fiber-type image capturer moving forward or backward. So a lateral hollowly cylinder scanning can be completed.

There can be other ramifications of the foregoing embodiment. For example, it needs not to be single mode fiber optic 100, and a group of single mode fiber optics (not shown) will also serve the purpose well. The group of single mode fiber optics can have different distances from the focusing module 300, so a scanning with different depth scanning information can be completed. The focusing module 300 can further be installed at a fixing base (not shown) to be fixed at the outer tube 700. Or the focusing module 300 can be fixed at the stator 450. The focusing module 300 can be spherical focusing lens, aspheric lens, gradient-index lens (GRIN lens), or microlens. And the GRIN lens or the microlens can further be integrated with the single mode fiber optic 100, to achieve a simpler design. (Please refer to FIG. 6.)

Moreover, the fiber-type image capturer can further include a fixing structure 730. The fixing structure 730 is connected or integrated to the outer tube 700, for fixing more securely of the single mode fiber optic 100 and the air inlet tube 710. The fixing structure 730 may own a hole near the center, so that the single mode fiber optic 100 and the fiber optic housing 200 can pass through and be fixed by the fixing structure 730. The fixing structure 730 can further own a small hole near the outer tube 700, so that the air inlet tube 710 can pass through the small hole and be fixed.

In the foregoing embodiment, the air outlet tube 720 can be replaced by another air outlet tube 750 at the outer tube 700 opposite to the air inlet tube 710. Or the air outlet tube 720 and 750 can both be adopted too. The air outlet tube 750 is not limited to tubular shape as shown in FIG. 5. The air outlet tube can be replaced by an simply an opening, as long as it vents air.

Figure 6:
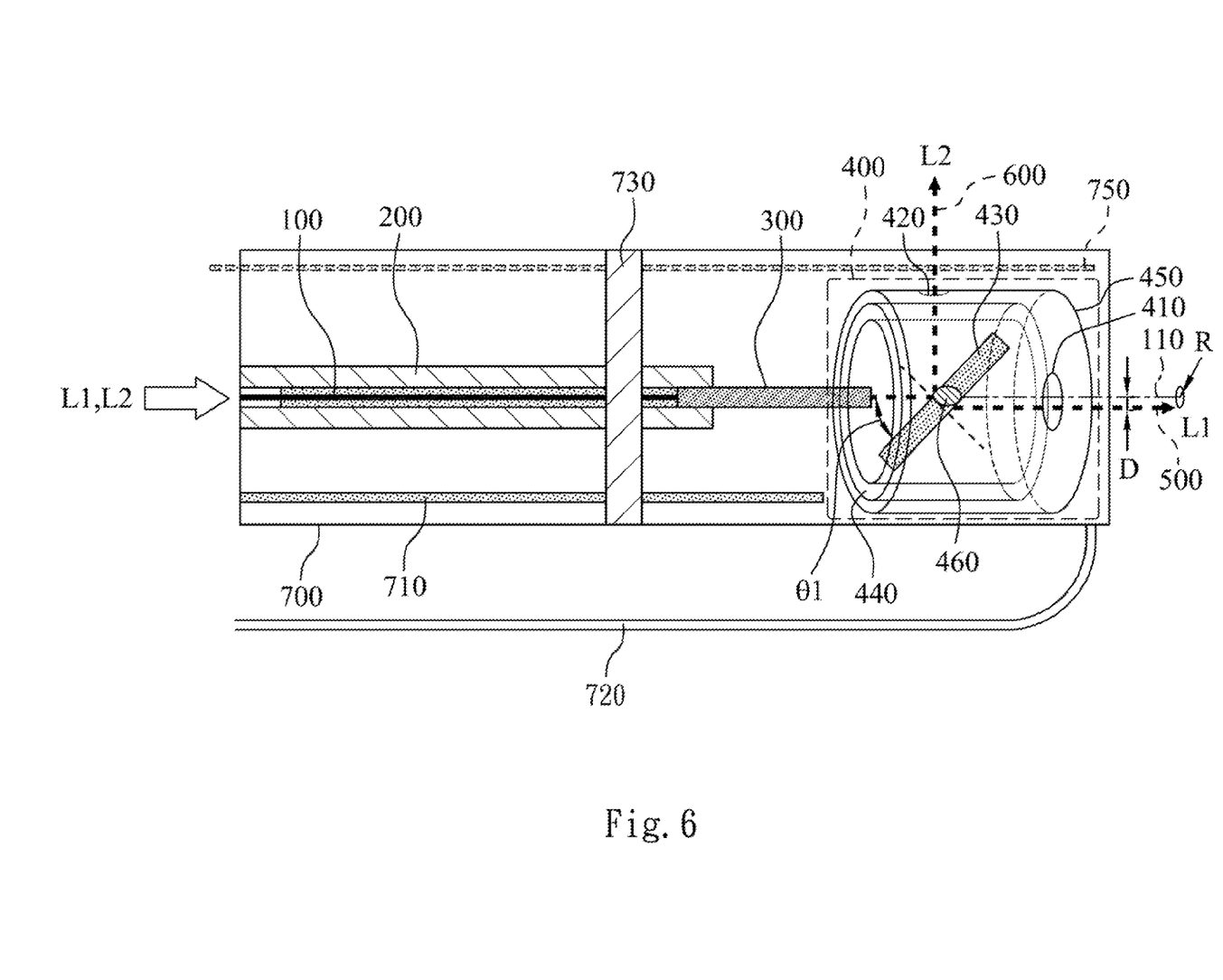
FIG. 6 is a side view of a fiber-type image capturing apparatus according to another embodiment of the present disclosure.

FIG. 6 is a side view of a fiber-type image capturer according to another embodiment of the present disclosure, which adopted a GRIN lens as the focusing module 300 and integrated with the single mode fiber optic 100. There are ramifications for the embodiment of FIG. 6 too, just like FIG. 5. The single mode fiber 100 can be replaced with a group of single mode fibers (not shown). And the group of single mode fibers can have different distances from the focusing module 300, so a scanning with different depth scanning information can be completed.

Figure 7:
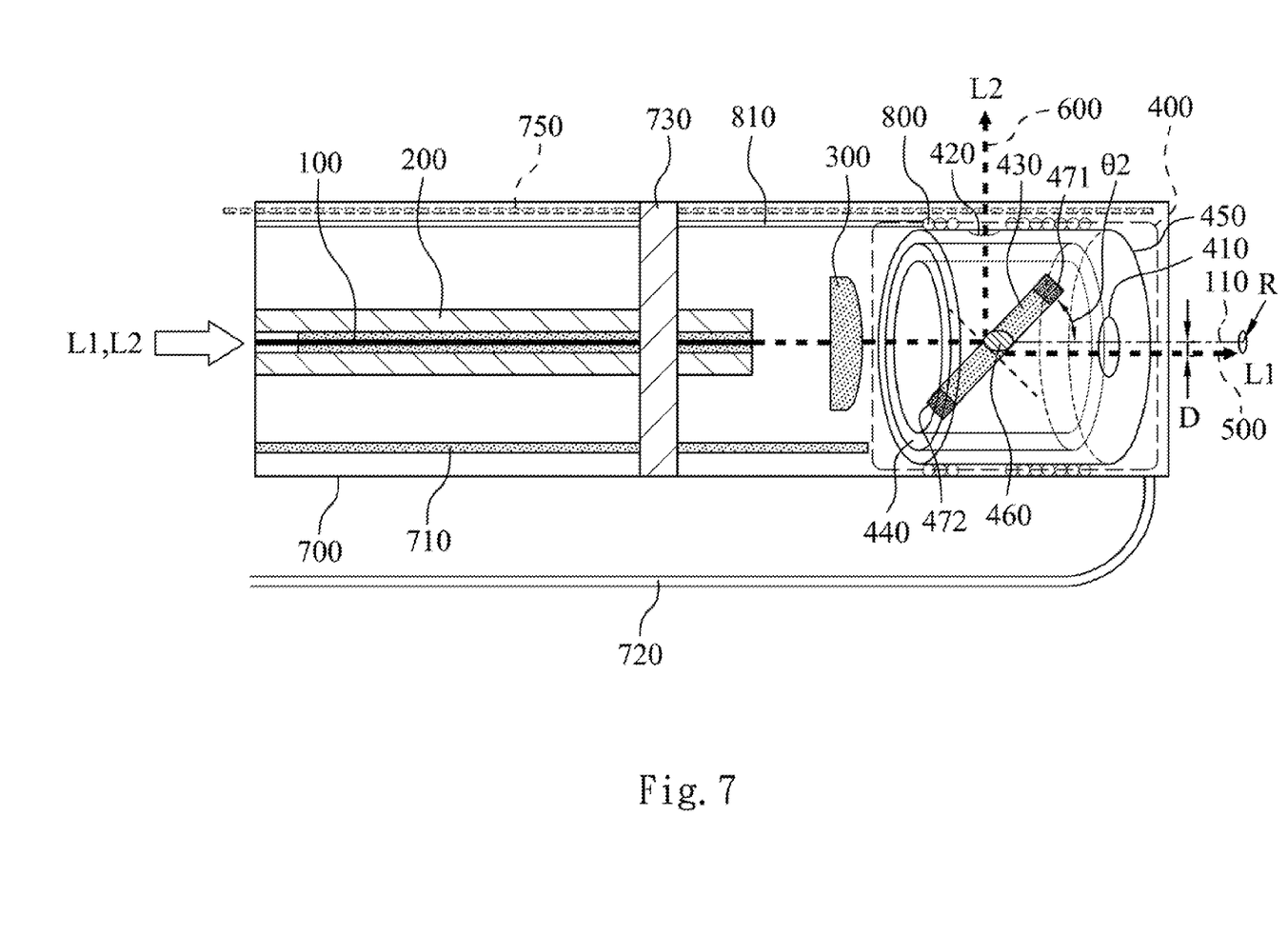
FIG. 7 is a side view of a fiber-type image capturing apparatus according to another embodiment of the present disclosure.

FIG. 7 is a side view of a fiber-type image capturer according to another embodiment of the present disclosure. Additional to the foregoing embodiment shown in FIG. 5, the fiber-type image capturer can further include a magnetic member 470 and a coil group 800. The magnetic member 470 is installed at the light path selector 430. The magnetic member 470 has magnets 471 and 472, being disposed with the north pole of magnet 471 and the south pole of magnet 472 in the opposite ends, respectively. The magnetic member 470 has a magnetic field intensity H. The coil group 800 is located between the stator 450 and the outer tube 700.

The operation of the embodiment is described as below. When current I is applied to the coil group 800 through a wire 810, from the principle of Electromagnetics, optical rotating module 400 will generate in a uniform magnetic field B inside the module. If the magnetic permeability of the hollow core part of the optical rotating module 400 is $m_0$, and the number of coil turns per unit length of the coil group 800 is n, then the magnetic field B is:

$$B = m_0 * n * I.$$

The magnetic field B interacts with the magnets 471 and 472 on the light path selector 430. If the angle between the magnetic field intensity vector H and the magnetic field vector B is θ', a potential energy U is produced. The quantity U of potential energy U is:

$$U = -H * B * \cos(\theta').$$

Applying minus gradient operation of potential energy U, a magnetic force can be obtained. The magnetic force rotates the light path selector 430 till the torsion of the stationary shaft 460 is balanced with the magnetic force. When the balance is reached between the torsion of the stationary shaft 460 and the magnetic force, the light path selector 430 stops rotating and stops at a inclination angle θ2. When the light path selector 430 changes its position to the inclination angle θ2, from. Snell's law and FIG. 3 and FIG. 4, the offset distance D is changed accordingly. And the inclination angle θ2 of the light path selector 430 can be controlled by the current I. Therefore, by controlling the current I the offset distance D can be changed and controlled. The radius R of the circular forward scanning path 500 equals to the offset distance D. So by controlling the current I, the radius R of the circular forward scanning path 500 can be changed and controlled.

Moreover, feeding air through the air inlet tube 710 can rotate the optical rotating module 400. Circular forward scanning with different radiuses R can be completed.

When performing lateral scanning along path 600, there can be no current applied to the coil group 800. So the light path selector 430 can maintain at a predetermined inclination angle θ2. The predetermined inclination angle θ2 can be 45 degrees. Then, the reflected light beam with wavelength L2 can pass the lateral light exit 420 perpendicularly to the base axis 110 and focus on a lateral scanning sample. At this time, the air inlet tube 710 can feeds air to stably rotate the optical rotating module 400. In this manner, the lateral scanning within a plane can be completed.

There can be a moving mechanism not shown) further added. The moving mechanism can bring the fiber-type image capturer moving forward or backward. So a lateral scanning within a cylinder can be completed. When performing the lateral scanning, keeping the inclination angle precisely at the predetermined θ2=45 degrees, can avoid additional optical aberration due to asymmetry. But, there is some tolerances, the tolerance within about 0 to 10 degrees can still be acceptable.

Furthermore, the coil group 800 doesn't need to be always installed between the stator 450 and the outer tube 700. As long as the coil group 800 is around the light path selector 430 and not interfere with other structure, the coil group 800 can be installed at many positions. For example, the coil group 800 can be located between the rotor 440 and the light path selector 430, or the coil group 800 can be located outside of the outer tube 700. There are ramifications for the embodiment of FIG. 7 too, just like FIG. 5 and FIG. 6. The single mode fiber optic 100 can be replaced with a group of single mode fiber optics (not shown). And the group of single mode fiber optics can have different distances from the focusing module 300, so a scanning with different depth scanning information can be completed.

According to the foregoing embodiments and examples, the advantages of the present disclosure are described as follows.

1. Being able to performing both forward scanning and lateral scanning using one fiber-type image capturing apparatus. This is convenient and easy to use for operating scanning.

2. Saving time from operating forward scanning and lateral scanning separately in a traditional manner, especially saving time from changing the scanning probe.

3. Simplifying the equipment.

4. Suit for medical scanning, since the fiber-type image capturing apparatus provided is small in size, non-contact style, and low driving voltage.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A fiber-type image capturing method comprising the steps of:
   selecting a light beam with a predetermined wavelength via a light source;
   providing an optical rotating module;
   passing the light beam through the optical rotating module for forming a forward scanning path and a lateral scanning path based on the predetermined wavelength of the light beam;
   rotating the forward scanning path and the lateral scanning path by the optical rotating module;
   illuminating the light beam through the rotated forward scanning path and the rotated lateral scanning path to a sample; and
   collecting scattered light from the sample to form a scanned image;
   wherein the forward scanning path is through optical refraction, and the lateral scanning path is through optical reflection.

2. A fiber-type image capturing apparatus, comprising:
   a fiber optic;
   an optical rotating module, connected to one end of the fiber optic, wherein the optical rotating module has a light forward exit and a light lateral exit, the optical rotating module comprising:
   a stator, fixed correspondingly to the fiber optic;
   a rotor, having a fan blade, wherein the fan blade pivotally connected to the stator; and
   a light path selector, installed at the rotor, wherein the light path selector has a forward scanning path and a lateral scanning path;
   an outer tube, wrapping or fixing the fiber optic and the optical rotating module;
   an air inlet hole, disposed at the outer tube, whereby the air inlet hole feeds the fan blade with air; and
   an air outlet hole, disposed at the outer tube, whereby the air outlet hole vents the air fed by the air inlet hole.

3. The fiber-type image capturing apparatus of claim 2, wherein the fiber optic is single mode fiber optic.

4. The fiber-type image capturing apparatus of claim 2, wherein the fiber optic is a fiber optic bundle.

5. The fiber-type image capturing apparatus of claim 2, further comprising:
   a coil group, located around the light path selector; and
   at least one magnetic pole, located at an end surface of the light path selector.

6. The fiber-type image capturing apparatus of claim 5, wherein the coil group is located between the optical rotating module and the outer tube.

7. The fiber-type image capturing apparatus of claim 5, wherein the coil group is located between the light path selector and the rotor.

8. The fiber-type image capturing apparatus of claim 2, wherein the light path selector guides the inputted light beam to the light forward exit or the light lateral exit based on the predetermined wavelength of the light beam.

9. The fiber-type image capturing apparatus of claim 2, wherein the light path selector is a plate having two opposite surfaces, wherein an included angle between the two surfaces is less than or equal to 10 degrees.

10. The fiber-type image capturing apparatus of claim 2, wherein the light path selector has a film coating.

11. The fiber-type image capturing apparatus of claim 2, further comprising:
    a stationary shaft, fixed to the rotor, wherein the light path selector is pivotally connected to the stationary shaft to be installed at the rotor.

12. The fiber-type image capturing apparatus of claim 2, further comprising:
    a focusing module, located between the fiber optic and the optical rotating module.

13. The fiber-type image capturing apparatus of claim 12, wherein the focusing module is spherical lens, aspherical lens, gradient-index lens, or microlens.

14. The fiber-type image capturing apparatus of claim 12, wherein the focusing module is integrated with the fiber optic.

15. The fiber-type image capturing apparatus of claim 2, further comprising:
    a fiber optic housing, wherein the fiber optic is disposed in the fiber optic housing.

16. The fiber-type image capturing apparatus of claim 15, further comprising:
    a fixing structure, for fixing the fiber optic and the fiber optic housing to the outer tube.

* * * * *